United States Patent
Hsiao et al.

(10) Patent No.: US 10,395,370 B2
(45) Date of Patent: Aug. 27, 2019

(54) METHOD AND WEARABLE APPARATUS FOR DISEASE DIAGNOSIS

(71) Applicant: National Taiwan University, Taipei (TW)

(72) Inventors: Hao-Ming Hsiao, Taipei (TW); Hsien-Li Kao, Taipei (TW); Kuang-Huei Lee, Taipei (TW); Dian-Ru Li, Taipei (TW)

(73) Assignee: National Taiwan University, Taipei (TW)

( * ) Notice: Subject to any disclaimer, the term of this patent is extended or adjusted under 35 U.S.C. 154(b) by 443 days.

(21) Appl. No.: 14/838,341

(22) Filed: Aug. 27, 2015

(65) Prior Publication Data
US 2016/0078622 A1    Mar. 17, 2016

(30) Foreign Application Priority Data

Sep. 16, 2014  (TW) .............................. 103131894 A

(51) Int. Cl.

| G06T 7/00 | (2017.01) |
|---|---|
| H04N 5/225 | (2006.01) |
| H04N 5/232 | (2006.01) |
| H04N 5/265 | (2006.01) |
| A61B 3/14 | (2006.01) |
| A61B 3/00 | (2006.01) |
| H04N 5/262 | (2006.01) |
| G06T 7/33 | (2017.01) |

(52) U.S. Cl.
CPC .......... *G06T 7/0016* (2013.01); *A61B 3/0041* (2013.01); *A61B 3/14* (2013.01); *G06T 7/33* (2017.01); *H04N 5/2252* (2013.01); *H04N 5/23293* (2013.01); *H04N 5/265* (2013.01); *H04N 5/2621* (2013.01); *G06T 2207/10016* (2013.01); *G06T 2207/10024* (2013.01); *G06T 2207/20016* (2013.01); *G06T 2207/30076* (2013.01)

(58) Field of Classification Search
CPC ..................................................... G06T 7/0016
See application file for complete search history.

(56) References Cited

U.S. PATENT DOCUMENTS

| 2006/0239530 A1* | 10/2006 | Oosawa | G06T 7/0012 382/130 |
| 2010/0021085 A1* | 1/2010 | Kabasawa | G06T 3/4084 382/300 |
| 2014/0072193 A1* | 3/2014 | Motomura | G06T 7/0012 382/128 |

(Continued)

*Primary Examiner* — Rowina J Cattungal
(74) *Attorney, Agent, or Firm* — JCIPRNET

(57) ABSTRACT

A method and a wearable apparatus for disease diagnosis are provided. The method is applied to the wearable apparatus with an image capturing unit and a display unit. In this method, a plurality of input images in a field of view of the wearable apparatus are captured by using the image capturing unit, wherein each of the input images contains an array of pixels. The variations of the pixel values in a time domain are analyzed. The pixel variations within a specific frequency range are magnified and the magnified pixel variations are added onto the original ones to generate an output image. The output image is overlapped with a current image in the field of view of the wearable apparatus and displayed on the display unit.

10 Claims, 6 Drawing Sheets

(56) References Cited

U.S. PATENT DOCUMENTS

| | | | | |
|---|---|---|---|---|
| 2014/0176751 A1* | 6/2014 | Kuzuya | ............... | G06T 3/4053 |
| | | | | 348/222.1 |
| 2014/0314333 A1* | 10/2014 | Takahashi | ............ | A61B 6/5258 |
| | | | | 382/264 |
| 2015/0068069 A1* | 3/2015 | Tran | ..................... | H04B 1/385 |
| | | | | 36/136 |
| 2017/0261750 A1* | 9/2017 | Wong | .................. | G02B 27/017 |

\* cited by examiner

METHOD AND WEARABLE APPARATUS FOR DISEASE DIAGNOSIS

CROSS-REFERENCE TO RELATED APPLICATION

This application claims the priority benefit of Taiwan application serial no. 103131894, filed on Sep. 16, 2014. The entirety of the above-mentioned patent application is hereby incorporated by reference herein and made a part of this specification.

BACKGROUND OF THE INVENTION

1. Field of the Invention

The invention is related to an image processing method and apparatus, and more particularly, to a method and a wearable apparatus for disease diagnosis.

2. Description of Related Art

In recent years, new image processing technology that processes images by using computer algorithms to analyze and process variations of the images in a time domain has been introduced. This technology uncovers subtle variations that are undetectable or difficult to observe with the naked eye. Low amplitude movements that are unrecognizable by the naked eye, or even color changes due to blood flowing through the face, may all be brought into a phase observable by the naked eye with the new image processing technology.

Currently, the scope of application for the new image processing technology is still in a developmental stage. For instance, in terms of engineering practice, the new image processing technology can be applied to observe the stability of buildings, and in terms of medical detection, the new image processing technology can be applied to observe the physiological actions of a test subject, such as respiration and heart rate. However, the scope of application has not been extended to instant disease diagnosis clinically yet.

SUMMARY OF THE INVENTION

The invention provides a method and a wearable apparatus for disease diagnosis which magnifies subtle variations on the surface of the human body and displays the magnified subtle variations on the wearable apparatus worn by a user, thereby realizing clinical disease diagnosis.

The method for disease diagnosis as provided by the invention is applicable to a wearable apparatus with an image capturing unit and a display unit. In this method, a plurality of input images in a field of view of the wearable apparatus is captured by using the image capturing unit, in which each of the input images contains an array of pixels. Then variations of the pixels in a time domain are analyzed so as to magnify the pixel variations within a specific frequency range, and the magnified pixel variations are added onto the original ones to generate an output image. Finally, the output image is overlapped with a current image in the field of view of the wearable apparatus and displayed on the display unit for disease diagnosis.

In an embodiment of the present invention, the step of analyzing the variations of the pixels in the time domain to magnify the pixel variations within the specific frequency range includes splitting the images into a plurality of frequency bands according to a spatial frequency distribution, and then magnifying the pixel variations within the specific frequency range, such as a heartbeat frequency.

In an embodiment of the present invention, the step of overlapping the output image with the current image in the field of view of the wearable apparatus includes capturing the current image in the field of view of the wearable apparatus by using the image capturing unit, analyzing at least one corresponding feature of both the output image and the current image, and then aligning the corresponding features according to the positions of each feature in the output image and the current image so as to overlap the output image on the current image.

In an embodiment of the present invention, after the step of adding the magnified pixel variations onto the original ones to generate the output image, the method further includes repeating the aforementioned steps to generate a plurality of magnified output images and subtracting a reference image from each of the other magnified output images to obtain a pixel value difference of each of the pixels by using one of the magnified output images as the reference image, then defining a vector according to a change in direction and a change in magnitude of the pixel value difference of each of the pixels in the other magnified output images and adding up the vectors of the pixels to generate a total vector, and finally determining an abnormality in the variations of the output images according to whether a value of the total vector exceeds a threshold. However, as long as the above-described object of determining an abnormality in the magnified pixel variations of the output images can be achieved, various types of signal processing methods and mathematical models for analyzing extracted data over time can be used in the regions of interest at a specific frequency range, and the present invention is not particularly limited thereto.

The wearable apparatus of the invention includes an image capturing unit, a display unit and a processing unit. The image capturing unit is configured to capture a plurality of input images in a field of view of the wearable apparatus, in which each of the input images contains an array of pixels. The processing unit is coupled to the image capturing unit and the display unit, and the processing unit includes an image magnification module and an image overlay module. The image magnification module is configured to analyze variations of the pixels of each of the input images captured by the image capturing unit in a time domain so as to magnify the pixel variations within a specific frequency range, and to add the magnified pixel variations onto the original ones to generate an output image. The image overlay module is configured to overlap the output image with a current image in the field of view of the wearable apparatus and to display the output image on the display unit for disease diagnosis.

In an embodiment of the present invention, the image magnification module includes a splitter, a filter and a magnifier. The splitter is configured to split the images into a plurality of frequency bands according to a spatial frequency distribution. The filter is configured to filter out or remove the pixel variations of the frequency bands outside the specific frequency range. The magnifier is configured to magnify the pixel variations of the frequency bands within the specific frequency range.

In an embodiment of the present invention, the image overlay module further includes a feature analyzer and a feature aligner. The feature analyzer is configured to analyze at least one corresponding feature of both the current image in the field of view of the wearable apparatus captured by the image capturing unit and the output image. The feature aligner is configured to align the corresponding features according to the positions of each feature in the output image and the current image so as to overlap the output image on the current image.

In an embodiment of the present invention, the image magnification module further reanalyzes the variations of the pixels in the input images captured by the image capturing unit in the time domain so as to magnify the pixel variations within the specific frequency range, and adds the magnified pixel variations onto the original ones to generate a plurality of output images.

In an embodiment of the present invention, the processing unit further includes an abnormality determination module, which uses one of the output images generated by the image magnification module as a reference image and subtracts the reference image from each of the other output images to obtain a pixel value difference of each of the pixels. The abnormality determination module defines a vector according to a change in direction and a change in magnitude of the pixel value difference of each of the pixels in the other output images, adds up the vectors of the pixels to generate a total vector, and determines an abnormality in the variations of the output images according to whether a value of the total vector exceeds a threshold. However, as long as the above-described object of determining an abnormality in the magnified pixel variations of the output images can be achieved, various types of signal processing methods and mathematical models for analyzing extracted data over time can be used in the regions of interest at a specific frequency range, and the present invention is not particularly limited thereto.

In an embodiment of the present invention, the disease diagnosis includes detections for cardiovascular and cerebrovascular diseases, diabetic autogenous arteriovenous fistula, peripheral vascular diseases, heart failure, and Parkinson's disease.

In view of the above, the wearable apparatus and the method for disease diagnosis of the present invention are directed to the images captured by the wearable apparatus. The images are split into various frequency bands according to the spatial frequency distribution thereof. After the images undergo time domain processing with respect to the frequency bands, a specific frequency range is then selected for analysis, thereby magnifying the subtle variations in the images. The magnified images may further be overlaid with the current image of the patient who is observed by medical personnel through the wearable apparatus. As a result, symptoms of the disease can be emphasized, and the clinical disease diagnosis can be achieved.

To make the aforementioned and other features and advantages of the application more comprehensible, several embodiments accompanied with drawings are described in detail as follows.

BRIEF DESCRIPTION OF THE DRAWINGS

The accompanying drawings are included to provide further understanding of the invention, and are incorporated in and constitute a part of this specification. The drawings illustrate embodiments of the invention and, together with the description, serve to explain the principles of the invention.

DESCRIPTION OF THE EMBODIMENTS

The invention combines image processing technology in a space domain and in a time domain, in which a subtle change in magnitude of an object captured by a wearable apparatus is brought into a phase observable by the naked eye via image processing and displayed on the wearable apparatus. When displaying a magnified image, the invention further performs feature analysis and comparison on the image and a current image captured by the wearable apparatus so as to overlap the image with an actual image observed by medical personnel through the wearable apparatus. By displaying the magnified symptom image on an actual object, medical personnel wearing the wearable apparatus may observe patient's symptoms immediately, thereby realizing clinical disease diagnosis.

Figure 1:
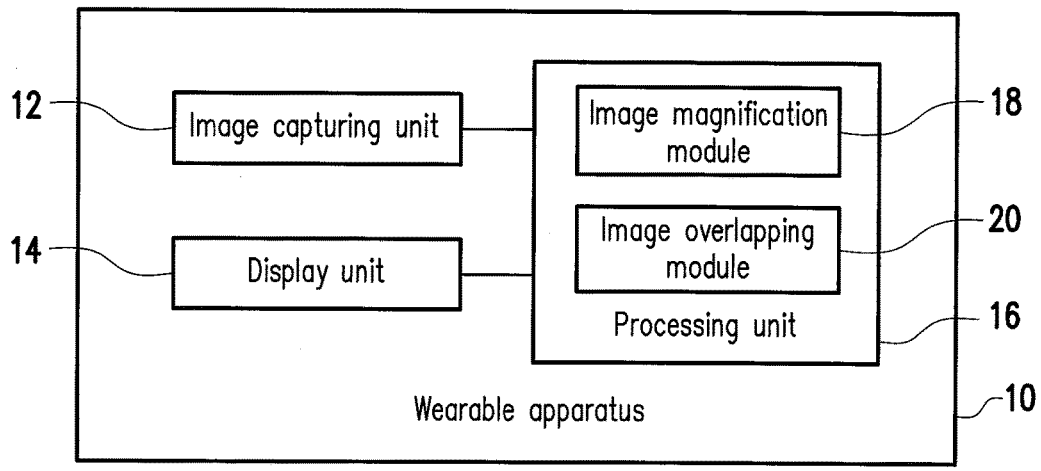
FIG. 1 is a block diagram illustrating a wearable apparatus according to an embodiment of the present invention.

FIG. 1 is a block diagram illustrating a wearable apparatus 10 according to an embodiment of the present invention. Referring to FIG. 1, the wearable apparatus 10 of the present embodiment is, for example, a device wearable on a human head, such as a pair of glasses, a pair of goggles, a headlamp, a helmet, or a hood, or a device wearable on a human upper extremity, such as a watch, a bracelet, or a mobile phone. The wearable apparatus 10 includes an image capturing unit 12, a display unit 14 and a processing unit 16, and the functions thereof are described as follows:

The image capturing unit 12 is, for example, disposed at the edge, the center or other locations of the main body of the wearable apparatus 10, and is configured to capture an image in a field of view of the wearable apparatus 10, such as an image of the patient being diagnosed. The image capturing unit 12 includes assembly components such as a lens, a shutter, or a photo-sensitive element. The photo-sensitive element is, for example, a Charge Coupled Device (CCD), a Complementary Metal-Oxide Semiconductor (CMOS) Device or so forth. The methods of image capturing are known to those skilled in the art and therefore are not further described herein. The image capturing unit 12 captures the image in the field of view of the wearable apparatus 10 when receiving a shutter signal triggered by the processing unit 16.

The display unit 14 is, for example, a Liquid Crystal Display (LCD), a Light-Emitting Diode (LED) Display, an Organic Light Emitting Display (OLED), an Electro-Phoretic Display (EPD), a micro-projection display using a LED light source or a laser light source, or other types of display.

The display unit 14 is coupled to the processing unit 16 for displaying images outputted by the processing unit 16. The display unit 14, for example, adopts a transparent or translucent display panel, and thus the user wearing the wearable apparatus 10 not only can see the image displayed by the display unit 14 but also can look through the display unit 14 to observe the image in the field of view of the wearable apparatus 10 behind the display unit 14.

The processing unit 16 is coupled to the image capturing unit 12 and the display unit 14, and is, for example, a Central Processing Unit (CPU) having a single-core or multi-cores, or programmable devices for general or special purposes such as a programmable microprocessor, a Digital Signal Processor (DSP), a programmable controller, an Application Specific Integrated Circuit (ASIC), other similar devices, or a combination thereof. In the present embodiment, the processing unit 16 may execute computer programs to perform a method for disease diagnosis according to an embodiment of the present invention.

The processing unit 16, for example, includes an image magnification module 18 and an image overlay module 20. These modules are, for example, hardware devices composed of logic circuit elements which are capable of executing disease diagnosis functions according to the embodiment of the present invention. These modules may also be programs stored in a storage medium (not shown) of the wearable apparatus 10 and may be loaded to the processing unit 16 to execute the disease diagnosis functions according to the embodiment of the present invention. Below, an exemplary embodiment is provided for explaining in detail the steps of the wearable apparatus 10 executing the disease diagnosis function.

Figure 2:
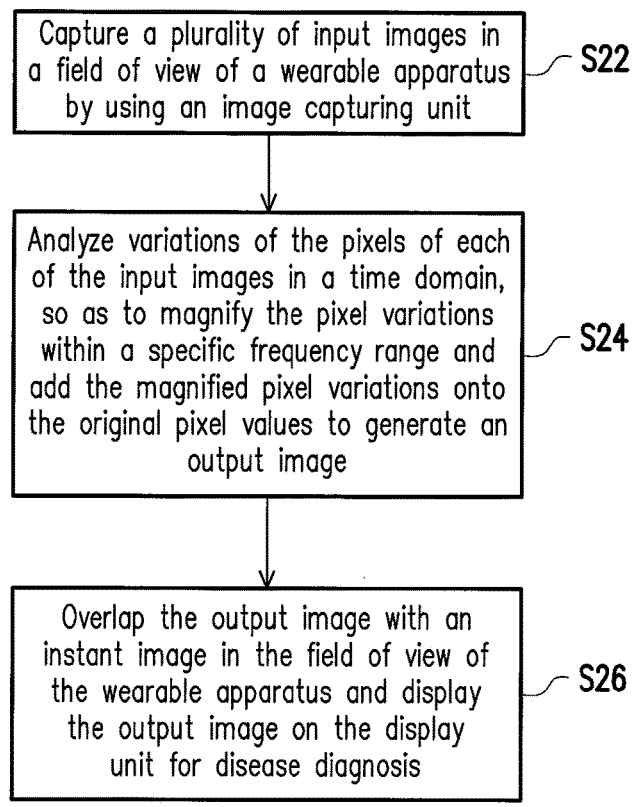
FIG. 2 is a flow chart illustrating a method for disease diagnosis according to an embodiment of the present invention.

In detail, FIG. 2 is a flow chart illustrating a method for disease diagnosis according to an embodiment of the present invention. Referring to FIG. 1 and FIG. 2, the method of the present embodiment is applicable to the aforementioned wearable apparatus 10, and detailed processes regarding the method of the present embodiment are provided below with reference to respective components of the wearable apparatus 10 in FIG. 1.

First, the image capturing unit 12 is used by the processing unit 16 to capture a plurality of input images in the field of view of the wearable apparatus 10 (step S22), wherein each of the input images includes an array of pixels.

Next, variations of the pixels of each of the input images captured by the image capturing unit 12 in a time domain are analyzed by the image magnification module 18 so as to magnify the pixel variations within a specific frequency range and add the magnified pixel variations onto the original pixel values to generate an output image (step S24). The image magnification module 18 splits each of the input images into different frequency bands according to a spatial frequency distribution thereof; then after the input images undergo time domain processing, unwanted noise may be filtered out and a specific frequency range of interest may be selected for subsequent analysis. Through this process, noise may be reduced and the pixel variations of other non-critical frequencies may be prevented from being magnified such that they cover the low amplitude image to be observed.

Figure 3:
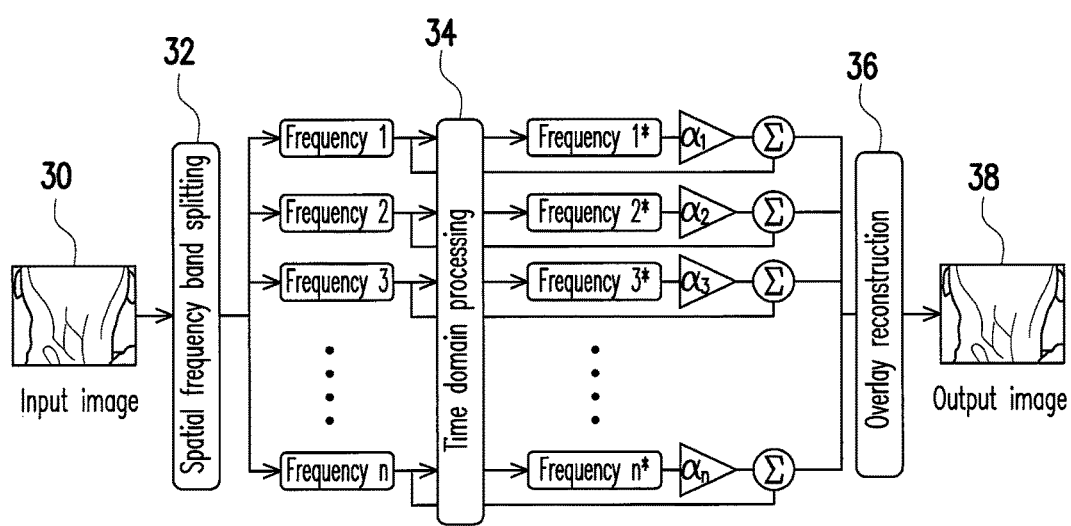
FIG. 3 is a schematic diagram illustrating the magnification of an image according to an embodiment of the present invention.

For instance, FIG. 3 is a schematic diagram illustrating the magnification of an image 30 according to an embodiment of the present invention. Referring to FIG. 3, in the present embodiment, the input image 30 is split into different spatial frequency bands 32; pixel variations in a specific frequency range are selected through a time domain processing 34; and finally, the pixel variations are multiplied with a magnification factor and magnified pixel variations are treated with an overlay reconstruction 36 to obtain an output image 38. For the variations in the pixel values with respect to the time domain, a magnification factor is used in the invention to magnify a change in magnitude of the image so as to ensure that subtle variations in the image are emphasized. For instance, the spatial wavelength of images is used to calculate the magnification factor with a linear function or other non-linear functions so as to emphasize the pixel variations in a frequency range of interest, thereby producing a favorable visual result; namely, a better way of showing the change in magnitude.

Figure 4:
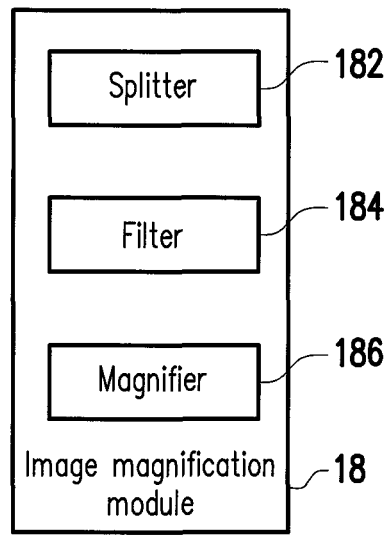
FIG. 4 is a block diagram illustrating an image magnification module according to an embodiment of the present invention.
Figure 5:
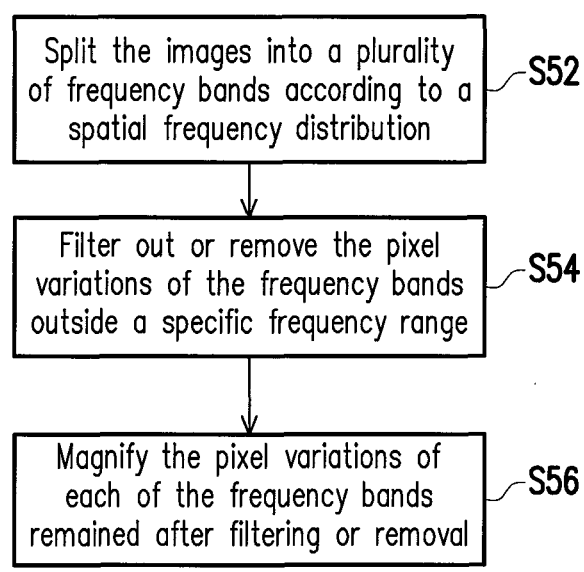
FIG. 5 is a flow chart illustrating an image magnification method according to an embodiment of the present invention.

Regarding the image processing, a complete method and an apparatus using the same are also provided in the invention for achieving image magnification functions. In detail, FIG. 4 is a block diagram illustrating an image magnification module according to an embodiment of the present invention. FIG. 5 is a flow chart illustrating an image magnification method according to an embodiment of the present invention. Specifically, FIG. 4 further illustrates detailed components of the image magnification module 18 shown in FIG. 1, which includes a splitter 182, a filter 184 and a magnifier 186. Details of the processes of the image magnification method of FIG. 5 are provided below with reference to various components shown in FIG. 4.

First, the images are split into a plurality of frequency bands according to a spatial frequency distribution by the splitter 182 (step S52). Next, the pixel variations of the frequency bands outside the specific frequency range are filtered out or removed by the filter 184 (step S54). That is, the image magnification module 18 keeps only the pixel variations of the frequency bands within the specific frequency range for the subsequent magnification processing, and the specific frequency range is, for example, a low amplitude range between 0.4 hertz and 4.0 hertz for magnifying low amplitude images.

Then the pixel variations of the frequency bands remaining in the specific frequency range are magnified by the magnifier 186 (step S56). For example, the magnifier 186 uses the pixel variations of the selected frequency band and selects a magnification factor adapted to multiply the pixel variations so as to achieve a magnification effect, wherein there is, for example, a linear relationship or non-linear relationship between the spatial wavelength and the magnification factor, but the invention is not limited thereto.

Figure 6A:
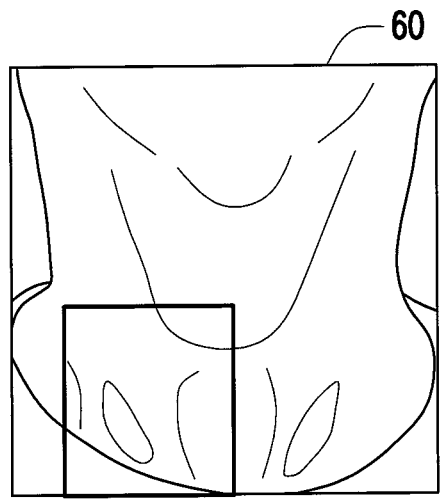
FIG. 6A to FIG. 6D illustrate implementations of the image magnification method according to an embodiment of the present invention.
Figure 6B:
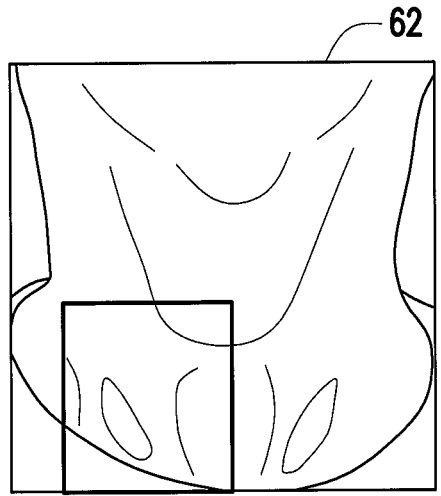
Figure 6C:
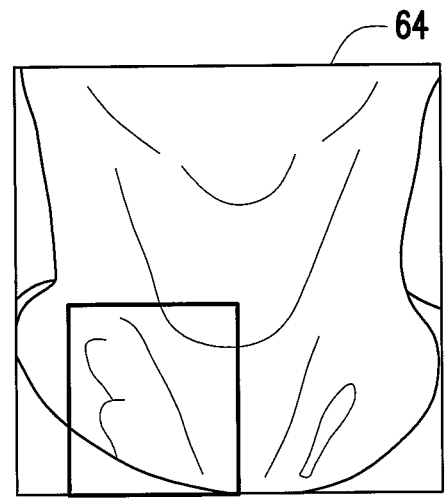
Figure 6D:
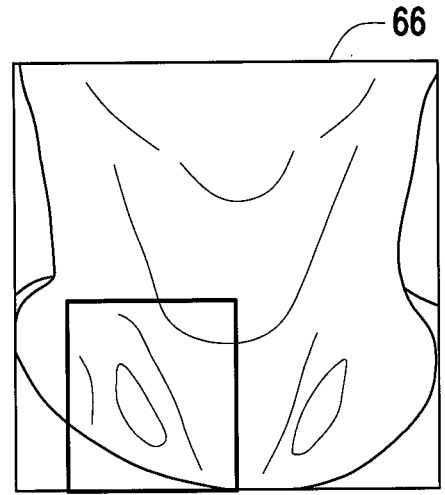

For instance, FIG. 6A to FIG. 6D illustrate implementations of the image magnification method according to an embodiment of the present invention. Using a neck inspection as an example, in the present embodiment, images 60, 62 shown in FIG. 6A and FIG. 6B are images respectively captured when the cervical vessel is in the vasodilation and vasoconstriction conditions. It can be known from the frames in the images 60, 62 shown in FIG. 6A and FIG. 6B that, when observing the test subject with the naked eye, it is difficult to observe the pulse fluctuation, and it is even more difficult to see the difference between vasodilation and vasoconstriction. However, after the images 60, 62 undergo the image magnification processing, a pulsation generated on the skin surface will become prominent during vasodilation and vasoconstriction. Even when blood flows through the vessel, subtle changes in color or movement at various spots may also be interpreted easily from the image. It can be known from the frames in images 64, 66 shown in FIG. 6C and FIG. 6D that, after performing the image processing for vascular pulsation, bulging and sagging motions on the skin surface will become apparent.

Also using the neck inspection as an example, in another embodiment, neck images of patients with or without stroke may be captured, respectively. In terms of visual observation by the naked eye, there is almost no difference between these images. However, after these images undergo the image magnification processing, vascular changes in the neck images of the patients with stroke will become prominent, while no obvious variation will be shown in the neck images of the patients without stroke. Hence, physicians may determine whether a person under examination is at risk of having or has had a stroke from the magnified images.

With the above method, pixel variations within a specific frequency range may be magnified to highlight low amplitude motions or color changes in the images, and thereby facilitate the identification of symptoms by medical personnel.

Referring to the processes shown in FIG. 2 again, after the image magnification module 18 generates the output image, the image overlay module 20 then overlaps the output image with the current image in the field of view of the wearable apparatus 10 and displays the output image on the display unit 14 for disease diagnosis (step S26). The image magnification module 18, for example, analyzes features of the output image and the current image and accordingly overlaps the output image with the current image so that the user may see a magnified output image in his/her field of view. The disease diagnosis, for example, may include detections of cardiovascular and cerebrovascular diseases, diabetic autogenous arteriovenous fistula, peripheral vascular diseases, heart failure, and Parkinson's disease. In addition, the method of the present embodiment may also be applied to other non-medical fields, such as lie detection, finding a hidden target from a stationary shielded object or a moving object or so forth, but the method of the present embodiment is not limited thereto.

Figure 7:
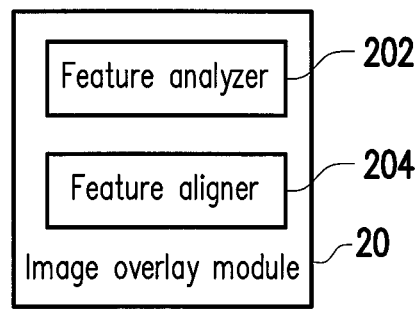
FIG. 7 is a block diagram illustrating an image overlay module according to an embodiment of the present invention.
Figure 8:
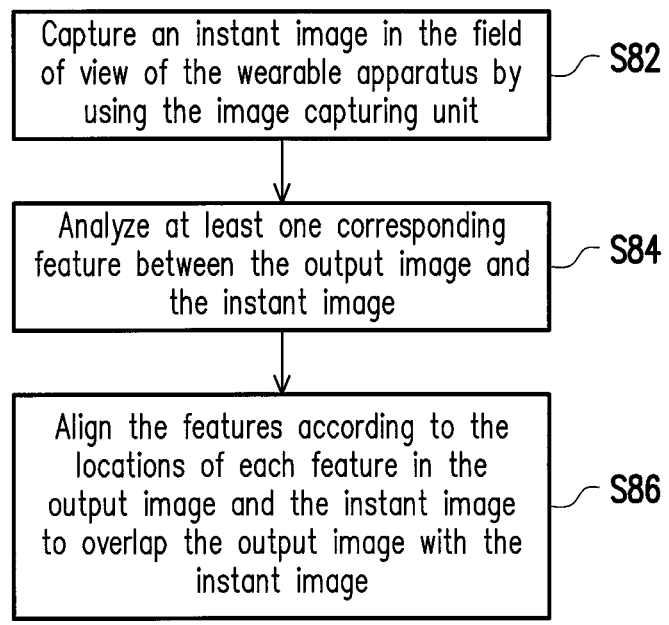
FIG. 8 is a flow chat illustrating an image overlay method according to an embodiment of the present invention.

In detail, FIG. 7 is a block diagram illustrating an image overlay module according to an embodiment of the present invention. FIG. 8 is a flow chart illustrating an image overlay method according to an embodiment of the present invention. FIG. 7 further illustrates detailed components of the image overlay module 20 shown in FIG. 1, which includes a feature analyzer 202 and a feature aligner 204. Below, processes regarding the image overlay method of FIG. 8 are described in detail with reference to various components shown in FIG. 7.

First, the image capturing unit 12 is used by the processing unit 16 to capture the current image in the field of view of the wearable apparatus 10 (step S82). Next, at least one corresponding feature of both the current image captured by the image capturing unit 12 and the output image is analyzed by the feature analyzer 202 (step S84). The feature analyzer 202, for example, uses an edge detection technique to analyze head, neck and facial contours of the test subject in the current image and the output image for identifying the facial features such as the eyes, the nose, the chin, and the ears. Then the feature aligner 204 may use an image overlay technique to align these features according to the locations of each feature in the output image and the current image so as to overlap the output image with the current image (step S86).

By overlapping the analyzed and magnified output image with the current image of the patient that is observed by the medical personnel through the wearable apparatus 10, symptoms of the patient may be magnified by means of unusual distortion, thereby allowing the medical personnel to identify the symptoms more clearly. The output image overlapping the current image may further be displayed or marked with animations or colors so that the symptoms observed by the physicians may appear to be different from the surrounding skin.

It is to be noted that, in addition to overlapping the magnified image with the current image for assisting medical personnel in identifying symptoms, the embodiment of the present invention may also identify the pixel variation in each spot of the magnified image and quantify the change in magnitude with respect to the time domain. With this quantitative indicator, the invention may further assist medical personnel in quickly determining and monitoring possible symptoms at an early stage. Details are further described in relation to the following embodiment.

Figure 9:
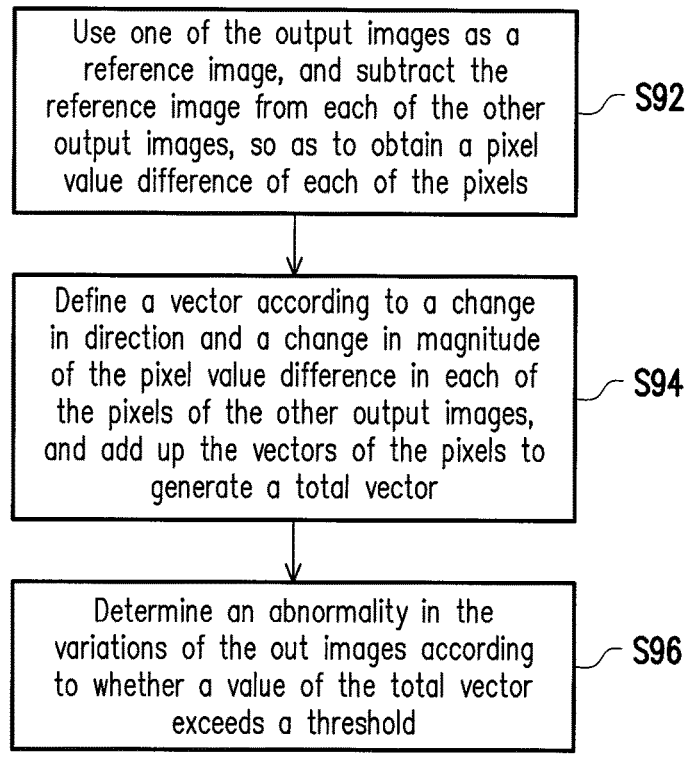
FIG. 9 is a flow chat illustrating an image variation determination method according to an embodiment of the present invention.

FIG. 9 is a flow chart illustrating an image variation determination method according to an embodiment of the present invention. Referring to FIG. 1 and FIG. 9, in the present embodiment, the variation of the pixels of the input images captured by the image capturing unit 12 are reanalyzed in the time domain through the image magnification module 18 so as to magnify the pixel variations of the frequency bands within the specific frequency range and to add the magnified pixel variations onto the original ones to generate a plurality of output images. Regarding the output images of the present embodiment, pixel variations in the output images are quantified by an abnormality determination module (not shown) in the processing unit 16 to obtain the quantitative indicator and to determine accordingly whether the test subject is at risk of certain diseases.

In detail, one of the output images generated by the image magnification module 18 is used as a reference image, and the reference image is subtracted from the other output images by the abnormality determination module, respectively, so as to obtain a pixel value difference of each of the pixels (step S92). Afterwards, a vector is defined according to a change in direction and a change in magnitude of the pixel value difference in each of the pixels of the output images by the abnormality determination module, and the vectors of the pixels are added up to generate a total vector (step S94). Last, the total vector may be quantified as a value, and an abnormality in the variations of the output images may be determined by the abnormality determination module according to whether the value exceeds a threshold (step S96). However, as long as the object of determining an abnormality can be achieved, various types of signal processing methods and mathematical models can be used, and the present invention is not particularly limited thereto.

Figure 10:
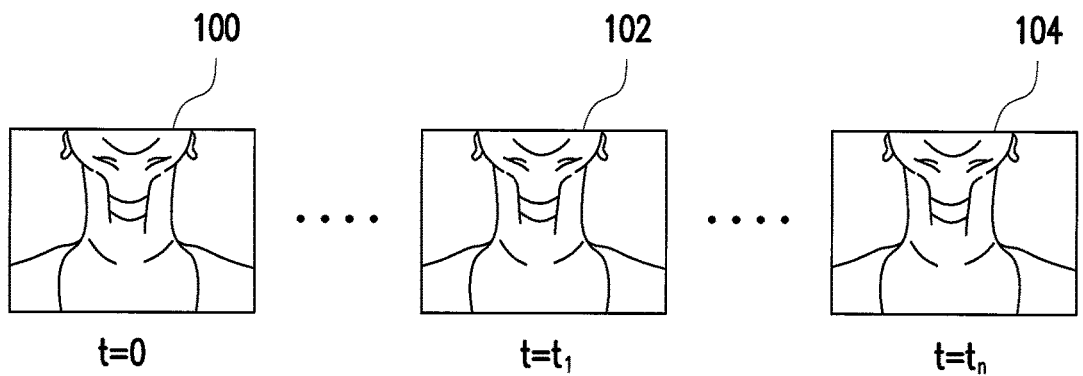
FIG. 10 illustrates an implementation of image variation determination method according to an embodiment of the present invention.

For instance, FIG. 10 illustrates an implementation of the image variation determination method according to an embodiment of the present invention. Referring to FIG. 10, the neck images of the test subject are used as examples in the present embodiment. Assuming an image 102 at time $t_1$ is the reference image, a differential value of each pixel value in each of the images may be obtained by subtracting image 102 at time $t_1$ from image 100 at time $t_0$ through image 104 at time $t_n$, respectively. Next, a vector is defined by the differential value of each of the images according to a change in the movement direction thereof, and the images from time $t_0$ to time $t_n$ are added up to perform a vector superposition for each pixel, respectively. The location, size and direction of a primary change in magnitude occurring on the neck of the test subject can be inferred from the length and the direction of the total vector, and thus connections between the variation and the test subject's physiological condition or the diseases may be found through the quantified value. For instance, the total vector may be quantified as a quantitative indicator and rated in levels of 1 to 10; if the level of the test subject exceeds 5, it indicates that the variation exceeds a standard variation and the test subject may be at risk of certain diseases.

The quantitative indicator can assist medical personnel in quickly determining and monitoring potential patients at an early stage and prevent physical illness alerts from being ignored, thereby significantly improving the chances of the patient being cured.

In summary, the method and the wearable apparatus for disease diagnosis of the invention, being capable of detecting the symptoms by merely using a camera to capture images and performing the image processing, have the advantages of non-invasive diagnosis and constitute a great improvement of the diagnostic process in terms of safety and convenience. If further combined with the characteristics of the wearable apparatus to directly display the processed image on the wearable apparatus and to further overlap the processed image with the current image viewed by medical personnel, the method and the wearable apparatus for disease diagnosis of the invention may assist medical personnel in quickly identifying symptoms. In addition, through establishing a quantitative indicator, medical personnel can quickly determine and monitor the potential patients at an early stage and prevent physical illness alerts from being ignored, thereby significantly improving the chances of the patient being cured.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for disease diagnosis, applicable to a wearable apparatus with an image capturing device and a display, the method comprising the following steps:
   capturing a plurality of input images in a field of view of the wearable apparatus by using the image capturing device, wherein each of the input images contains an array of pixels;
   analyzing variations of the pixels between each of the input images in a space domain and in a time domain to magnify pixel variations within a specific frequency range, and adding the magnified pixel variations onto the original pixel values to generate an output image, wherein the pixel at a same location in each of the input images forms a vector in the time domain for pixel variation analysis,
   wherein the step of analyzing the variations of the pixels between each of the input images in the space domain and in the time domain to magnify the pixel variations within the specific frequency range comprises:
      splitting the images into a plurality of frequency bands according to a spatial frequency distribution;
      filtering out or removing pixel variations of frequency bands of the plurality of frequency bands outside of the specific frequency range;
      magnifying the pixel variations of the frequency bands within the specific frequency range; and
      selecting a magnification factor adapted for multiplying the pixel variations so as to achieve a magnification of the pixel variations within the specific frequency range; and
   overlapping the output image with a current image in the field of view of the wearable apparatus, and displaying the output image on the display for disease diagnosis.

2. The method for disease diagnosis as claimed in claim 1, wherein the step of overlapping the output image with the current image in the field of view of the wearable apparatus comprises:
   capturing the current image in the field of view of the wearable apparatus by using the image capturing device;
   analyzing at least one corresponding feature of both the output image and the current image; and
   aligning the corresponding features according to the positions of each feature in the output image and the current image so as to overlap the output image on the current image.

3. The method for disease diagnosis as claimed in claim 1, wherein after the step of adding the magnified pixel variations onto the original ones to generate the output image, the method further comprises:
   repeating the aforementioned steps to generate a plurality of magnified output images;
   using one of the magnified output images as a reference image and subtracting the reference image from each of the other magnified output images to obtain a pixel value difference of each of the pixels;
   defining a vector according to a change in direction and a change in magnitude of the pixel value difference of each of the pixels in the other magnified output images, and adding up the vectors of the pixels to generate a total vector; and
   determining an abnormality in the variations of the output images according to whether a value of the total vector exceeds a threshold.

4. The method for disease diagnosis as claimed in claim 3, wherein the step of determining the abnormality in the variations of the output images according to whether the value of the total vector exceeds the threshold comprises:
   quantifying the total vector as a quantitative indicator according to a length and a direction of the total vector; and
   determining the abnormality in the variations of the output images according to whether the quantitative indicator exceeds the threshold.

5. The method for disease diagnosis as claimed in claim 1, wherein the disease diagnosis comprises detections for cardiovascular and cerebrovascular diseases, diabetic autogenous arteriovenous fistula, peripheral vascular diseases, heart failure, and Parkinson's disease.

6. A wearable apparatus, comprising:
   an image capturing device, configured to capture a plurality of input images in a field of view of the wearable apparatus, in which each of the input images contains an array of pixels;
   a display device; and
   a processor, coupled to the image capturing device and the display device, and configured to:
      analyze variations of the pixels between each of the input images captured by the image capturing device in a space domain and in a time domain so as to magnify pixel variations within a specific frequency range, and adding the magnified pixel variations onto the original pixel values to generate an output image, wherein the pixel at a same location in each of the input images forms a vector in the time domain for pixel variation analysis,
      wherein the processor is further configured to:
         split the images into a plurality of frequency bands according to a spatial frequency distribution;

filter out or remove pixel variations of frequency bands of the plurality of frequency bands outside the specific frequency range;

magnify the pixel variations of the frequency bands within the specific frequency range; and select a magnification factor adapted for multiplying the pixel variations so as to achieve a magnification of the pixel variations within the specific frequency range; and overlap the output image with a current image in the field of view of the wearable apparatus and display the output image on the display device for disease diagnosis.

7. The wearable apparatus as claimed in claim 6, wherein the processor is further configured to:

analyze at least one corresponding feature of both the current image in the field of view of the wearable apparatus captured by the image capturing device and the output image; and align the corresponding features according to the positions of each feature in the output image and the current image so as to overlap the output image on the current image.

8. The wearable apparatus as claimed in claim 6, wherein the processor further reanalyzes the variations of the pixels in the input images captured by the image capturing device in the time domain so as to magnify the pixel variations within the specific frequency range, and adds the magnified pixel variations onto the original pixel values to generate a plurality of output images.

9. The wearable apparatus as claimed in claim 8, wherein the processor is further configured to:

use one of the output images as a reference image and subtracting the reference image from each of the other output images to obtain a pixel value difference of each of the pixels, define a vector according to a change in direction and a change in magnitude of the pixel value difference of each of the pixels in the other output images and adding up the vectors of the pixels to generate a total vector, and determine an abnormality in the variations of the output images according to whether a value of the total vector exceeds a threshold.

10. The wearable apparatus as claimed in claim 6, wherein the disease diagnosis comprises detections for cardiovascular and cerebrovascular diseases, diabetic autogenous arteriovenous fistula, peripheral vascular diseases, heart failure, and Parkinson's disease.

* * * * *